(12) United States Patent
Lord (10) Patent No.: US 10,278,421 B2
(45) Date of Patent: May 7, 2019

(54) ELECTRONIC VAPOR PROVISION DEVICE

(71) Applicant: NICOVENTURES HOLDINGS LIMITED, London (GB)

(72) Inventor: Christopher Lord, London (GB)

(73) Assignee: NICOVENTURES HOLDINGS LIMITED, London (GB)

( * ) Notice: Subject to any disclaimer, the term of this patent is extended or adjusted under 35 U.S.C. 154(b) by 0 days.

(21) Appl. No.: 14/415,510

(22) PCT Filed: Jul. 15, 2013

(86) PCT No.: PCT/EP2013/064953
§ 371 (c)(1),
(2) Date: Jan. 16, 2015

(87) PCT Pub. No.: WO2014/012907
PCT Pub. Date: Jan. 23, 2014

(65) Prior Publication Data
US 2015/0201675 A1    Jul. 23, 2015

(30) Foreign Application Priority Data
Jul. 16, 2012    (GB) .................................. 1212608.2

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC .... A24F 47/002; A24F 47/004; A24F 47/006; A24F 47/008
See application file for complete search history.

(56) References Cited

U.S. PATENT DOCUMENTS

2003/0063902 A1    4/2003  Pedrotti
2009/0126745 A1*   5/2009  Hon ...................... A24F 47/008
                                                         131/273
(Continued)

FOREIGN PATENT DOCUMENTS

CA          2720293 A1    11/2009
CA          2641869 A1     5/2010
(Continued)

OTHER PUBLICATIONS

WO 0028842(Machine Translation) [online], [retrieved on Sep. 14, 2015], retrieved from Espacenet (http://worldwide.espacenet.com/?locale=en_EP).*

(Continued)

*Primary Examiner* — Michael H. Wilson
*Assistant Examiner* — Dionne W. Mayes
(74) *Attorney, Agent, or Firm* — Patterson Thuente Pedersen, PA (57) ABSTRACT

An electronic vapor provision device comprising a power cell and a vaporizer, wherein the vaporizer comprises a heater and a vaporization cavity, wherein the vaporizer further comprises an airflow channeler configured, in use, to channel airflow over the heater.

32 Claims, 8 Drawing Sheets

(51) Int. Cl.
*A61M 11/04* (2006.01)
*A61M 16/00* (2006.01)

(52) U.S. Cl.
CPC ............ *A61M 2016/0021* (2013.01); *A61M 2016/0039* (2013.01); *A61M 2205/3375* (2013.01); *A61M 2205/3653* (2013.01); *A61M 2205/8206* (2013.01); *A61M 2206/16* (2013.01)

(56) References Cited

U.S. PATENT DOCUMENTS

| | | | |
|---|---|---|---|
| 2012/0111347 A1* | 5/2012 | Hon | .......... A24F 47/008 131/329 |
| 2015/0157055 A1 | 6/2015 | Lord | |
| 2015/0196058 A1 | 7/2015 | Lord | |
| 2016/0353804 A1 | 12/2016 | Lord | |

FOREIGN PATENT DOCUMENTS

| | | | | |
|---|---|---|---|---|
| CN | 201051862 | Y | 4/2008 | |
| CN | 201079011 | Y | 7/2008 | |
| CN | 201104488 | Y | 8/2008 | |
| CN | 201104588 | Y | 8/2008 | |
| CN | 105142443 | | 12/2015 | |
| DE | 19854009 | A1 | 5/2000 | |
| EP | 0430559 | A2 | 6/1991 | |
| EP | 2022349 | A1 | 2/2009 | |
| EP | 2319334 | * | 5/2011 | .......... A24F 47/008 131/273 |
| EP | 2319334 | A1 | 5/2011 | |
| EP | 2404515 | A1 | 1/2012 | |
| JP | 2012-29633 | | 2/2012 | |
| RU | 2297781 | C1 | 4/2007 | |
| RU | 2450780 | C2 | 5/2012 | |
| SU | 1641182 | A3 | 4/1991 | |
| UA | 89752 | C2 | 3/2010 | |
| UA | 67598 | U | 2/2012 | |
| WO | WO0028842 | * | 5/2000 | .......... A24F 47/006 |
| WO | 2007078273 | A1 | 7/2007 | |
| WO | WO 2009/132793 | A1 | 11/2009 | |
| WO | 2011124033 | A1 | 10/2011 | |
| WO | WO2011124033 | * | 10/2011 | .......... A24F 47/008 131/273 |
| WO | WO 2011/160788 | A1 | 12/2011 | |

OTHER PUBLICATIONS

International Search Report and Written Opinion, dated Oct. 11, 2013, for Application No. PCT/EP2013/064953, filed Jul. 15, 2013.
International Preliminary Report on Patentability, dated Oct. 30, 2014, for Application No. PCT/EP2013/064953, filed Jul. 15, 2013.
Japanese Office Action, Application No. 2015-522066, 3 pages, dated Dec. 9, 2015.
Canadian Office Action, Application No. 2,878,977, dated Jan. 22, 2016, 6 pages.
Russian Search Report, Application No. 2015 101 747, dated Jun. 17, 2016.
Ukraine Decision to Grant, Application No. a 2015 00322, dated Oct. 29, 2015, 5 pages.
Chinese Search Report, Application No. 2013800380964, dated Jul. 11, 2016, 2 pages.
Chinese Office Action, Chinese Application No. 201380038096.4, dated Jul. 19, 2016, 6 pages.
Korean Office Action, Application No. KR20157003703, dated Sep. 12, 2016, 12 pages.

* cited by examiner

ELECTRONIC VAPOR PROVISION DEVICE

CLAIM FOR PRIORITY

This application is the National Stage of International Application No. PCT/EP2013/064953, filed Jul. 15, 2013, which in turn claims priority to and benefit of United Kingdom Patent Application No. 1212608.2, filed Jul. 16, 2012. The entire contents of the aforementioned applications are herein expressly incorporated by reference.

TECHNICAL FIELD

The specification relates to electronic vapour provision devices.

BACKGROUND

Electronic vapour provision devices are typically cigarette-sized and function by allowing a user to inhale a nicotine vapour from a liquid store by applying a suction force to a mouthpiece. Some electronic vapour provision devices have an airflow sensor that activates when a user applies the suction force and causes a heater coil to heat up and vaporise the liquid. Electronic vapour provision devices include electronic cigarettes.

SUMMARY

In an embodiment there is provided an electronic vapour provision device comprising a power cell and a vaporiser, where the vaporiser comprises a heating element and a vaporisation cavity, wherein the vaporiser further comprises an airflow channeler configured in use to channel airflow over the heating element.

The airflow channeler may be configured to focus the airflow over the heating element or a region of the heating element. Moreover, the airflow channeler may form part of a heating element support. Furthermore, the electronic vapour provision device may comprise a mouthpiece section and the vaporiser may be part of the mouthpiece section.

In another embodiment there is provided a vaporiser for use in an electronic vapour provision device, comprising a heating element and an airflow channeler configured to channel airflow over the heating element.

In another embodiment there is provided an electronic vapour provision device comprising a heating element coil; a liquid store for providing liquid to be vaporised by the heating element; an air outlet for vaporised liquid from the heating element; and an airflow channeler configured to obstruct airflow within the coil and to direct the airflow to one or more parts of the coil surface. The device may for example comprise a power cell for powering the heating element.

BRIEF DESCRIPTION OF THE DRAWINGS

For a better understanding of the disclosure, and to show how example embodiments may be carried into effect, reference will now be made to the accompanying drawings in which.

DETAILED DESCRIPTION

In a first aspect of the present invention there is provided an electronic vapour provision device comprising a power cell and a vaporiser, where the vaporiser comprises a heating element and a vaporisation cavity, wherein the vaporiser further comprises an airflow channeler configured to channel airflow over the heating element. The electronic vapour provision device may be an electronic cigarette.

The vaporiser acts to vaporise liquid. When liquid is vaporised by the vaporiser, the resulting vapour is carried away by the airflow and inhaled by the user. Channeling the airflow over the heating element increases the rate at which vapour is carried away. This can lead to a more efficient vapour release.

The airflow channeler may be configured to focus the airflow over the heating element. By focusing the airflow over the heating element, the device becomes more efficient at carrying away vapour from the vaporiser. The device may therefore require less airflow and less suction effort by the user.

The airflow channeler may be configured to channel airflow over the surface of the heating element. Moreover, the airflow channeler may be configured to channel airflow along the length of the heating element. Channeling the airflow along the length of the heating element ensures that increased vapour removal occurs along the entire heating element.

The airflow channeler may be configured to focus airflow in a region of the heating element. Moreover, the airflow channeler may be configured to focus airflow in an end region of the heating element. For example, the airflow channeler may be configured to focus airflow in a central region of the heating element or at two or more points along the heating element. Furthermore the airflow channeler may be configured to create an airflow gradient over the heating element.

Liquid may be transferred onto the vaporiser heating element but this transfer may not be uniform along the length of the heating element. Thus, it may be advantageous to channel airflow to regions of the heating element where there is more liquid to be vaporised.

The airflow channeler may be situated within the vaporisation cavity. Moreover, the airflow channeler may provide an obstruction in the vaporisation cavity such that airflow is channeled over the heating element.

The airflow channeler may be situated outside of the vaporisation cavity or may form part of a wall of the vaporisation cavity. Moreover, the airflow channeler may be situated within the heating element.

An obstruction in the vaporisation cavity means that the airflow will flow around the obstruction and can be directed towards the heating element. When the airflow path is within the heating element, an airflow channeler situated within the heating element is able to direct the airflow to the heating element surface for increased efficiency.

The airflow channeler may be situated outside of the heating element.

The airflow channeler may be elongated in the direction of the longitudinal coil axis. Furthermore, the airflow channeler may be cylindrical. Part of the airflow channeler may comprise a conical shape. For example, the airflow channeler may be substantially conical or frusto-conical.

The airflow channeler may comprise a wider end and a narrower end and may be configured such that air is drawn towards the wider end. Alternatively, the airflow channeler may comprises a wider end and a narrower end and the airflow channeler may be configured such that air is drawn towards the narrower end.

The airflow channeler may be shaped so as to bulge in a region. For example, the airflow channeler may be shaped so as to bulge in a central region or in two or more places along its length.

The cross-sectional shape of the airflow channeler may be a polygon, such as a square. Moreover, the airflow channeler may comprise a spiral shape.

The heating element may be a heating coil, such as a wire coil.

The airflow channeler may be configured to focus airflow over the heating coil turns. The airflow channeler may be configured to focus airflow along the length of the coil. The airflow channeler may be configured to focus airflow on the end of the coil. The airflow channeler may be configured to focus airflow on the inside of the coil. The airflow channeler may be configured to focus airflow on the outside of the coil. The airflow channeler may be configured to focus airflow through the coil turns. The airflow channeler may be configured to spiral airflow over the coil.

The heating element may be not supported on its inside. The vaporiser may further comprise a heating element support. The heating element support may be a liquid store. Moreover, the heating element may be on the inside of the heating element support.

Having a separate heating element and support allows a finer heating element to be constructed. This is advantageous because a finer heating element can be more efficiently heated. By having the heating element on the inside of the support means that a much smaller and narrower heating element can be used since space is not needed inside the heating element to house the support. This enables a much larger and therefore stronger support to be used.

One or more gaps may be provided between the heating element and the heating element support. Moreover, the heating element may be in contact with the heating element support at points along the length of the support.

The airflow channeler may form part of the heating element support. Alternatively, the airflow channeler may not form part of the heating element support.

The airflow channeler may not be in contact with the heating element. By having an airflow channeler that is not in contact with the heating element, the airflow channeler does not impede the heating surface of the heating element.

The electronic vapour provision device may further comprise a mouthpiece section and the vaporiser may be part of the mouthpiece section. The heating element support may substantially fill the mouthpiece section.

Since the support is on the outside of the coil and can act as a liquid store, a liquid store container is not needed in addition to the liquid store and the heating element support can fill the mouthpiece section to give greater storage capacity and a more efficient device.

Figure 1:
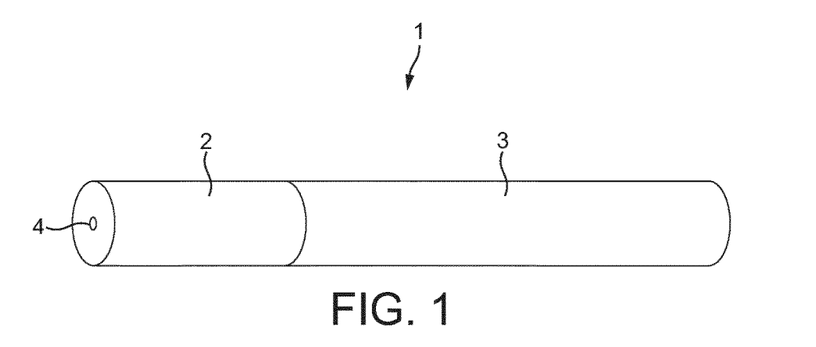
FIG. 1 is a side perspective view of an electronic cigarette.

Referring to FIG. 1 there is shown an embodiment of the electronic vapour provision device 1 in the form of an electronic cigarette 1 comprising a mouthpiece 2 and a body 3. The electronic cigarette 1 is shaped like a conventional cigarette having a cylindrical shape. The mouthpiece 2 has an air outlet 4 and the electronic cigarette 1 is operated when a user places the mouthpiece 2 of the electronic cigarette 1 in their mouth and inhales, drawing air through the air outlet 4. Both the mouthpiece 2 and body 3 are cylindrical and are configured to connect to each other coaxially so as to form the conventional cigarette shape.

Figure 2:
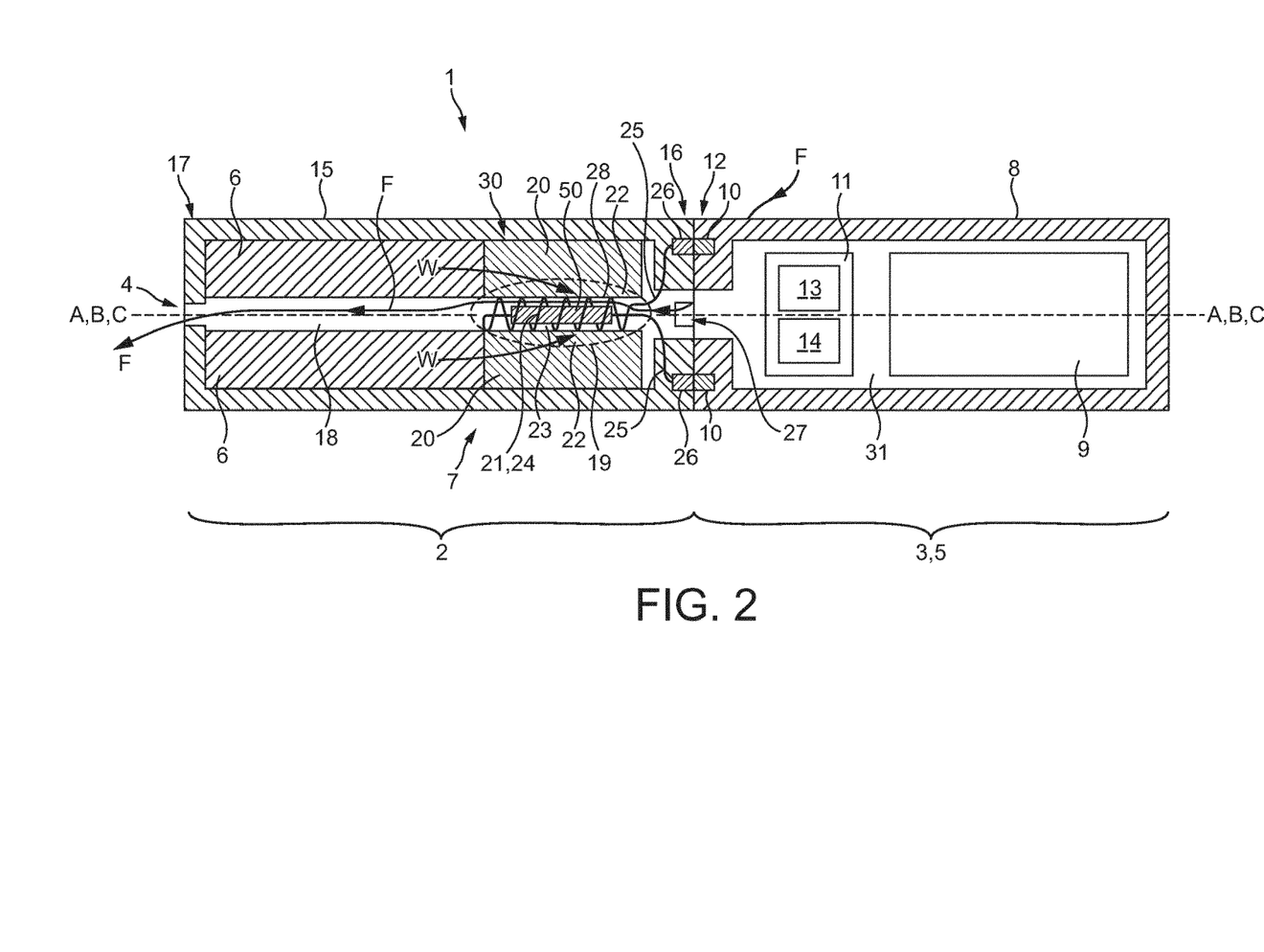
FIG. 2 is a schematic sectional view of an electronic cigarette having a parallel coil.

FIG. 2 shows an example of the electronic cigarette 1 of FIG. 1. The body 3 is referred to herein as a battery assembly 5, and the mouthpiece 2 includes a liquid store 6 and a vaporiser 7. The electronic cigarette 1 is shown in its assembled state, wherein the detachable parts 2, 5 are connected. Liquid wicks from the liquid store 6 to the vaporiser 7. The battery assembly 5 provides electrical power to the vaporiser 7 via mutual electrical contacts of the battery assembly 5 and the mouthpiece 2. The vaporiser 7 vaporises the wicked liquid and the vapour passes out of the air outlet 4. The liquid may for example comprise a nicotine solution.

The battery assembly 5 comprises a battery assembly casing 8, a power cell 9, electrical contacts 10 and a control circuit 11.

The battery assembly casing 8 comprises a hollow cylinder which is open at a first end 12. For example, the battery assembly casing 8 may be plastic. The electrical contacts 10 are located at the first end 12 of the casing 8, and the power cell 9 and control circuit 11 are located within the hollow of the casing 8. The power cell 9 may for example be a Lithium Cell.

The control circuit 11 includes an air pressure sensor 13 and a controller 14 and is powered by the power cell 9. The controller 14 is configured to interface with the air pressure sensor 13 and to control provision of electrical power from the power cell 9 to the vaporiser 7, via the electrical contacts 10.

The mouthpiece 2 further includes a mouthpiece casing 15 and electrical contacts 26. The mouthpiece casing 15 comprises a hollow cylinder which is open at a first end 16, with the air outlet 4 comprising a hole in the second end 17 of the casing 15. The mouthpiece casing 15 also comprises an air inlet 27, comprising a hole near the first end 16 of the casing 15. For example, the mouthpiece casing may be formed of aluminium.

The electrical contacts 26 are located at the first end of the casing 15. Moreover, the first end 16 of the mouthpiece casing 15 is releasably connected to the first end 12 of the battery assembly casing 8, such that the electrical contacts 26 of the mouthpiece 2 are electrically connected to the electrical contacts 10 of the battery assembly 5. For example, the device 1 may be configured such that the mouthpiece casing 15 connects to the battery assembly casing 8 by a threaded connection.

The liquid store 6 is situated within the hollow mouthpiece casing 15 towards the second end 17 of the casing 15. The liquid store 6 comprises a cylindrical tube of porous material saturated in liquid. The outer circumference of the liquid store 6 matches the inner circumference of the mouthpiece casing 15. The hollow of the liquid store 6 provides an air passageway 18. For example, the porous material of the liquid store 6 may comprise foam, wherein the foam is substantially saturated in the liquid intended for vaporisation.

The vaporiser 7 comprises a vaporisation cavity 19, a heating element support 20, a heating element 21 and an airflow channeler 50.

The vaporisation cavity 19 comprises a region within the hollow of the mouthpiece casing 15 in which liquid is vaporised. The heating element 21 and a portion 22 of the support 20 are situated within the vaporisation cavity 19.

The heating element support 20 is configured to support the heating element 21 and to facilitate vaporisation of liquid by the heating element 21. The heating element support 20 is an outer support and is illustrated in FIGS. 4 to 7. The support 20 comprises a hollow cylinder of rigid, porous material and is situated within the mouthpiece casing 15, towards the first end 16 of the casing 15, such that it abuts the liquid store 6. The outer circumference of the support 20 matches the inner circumference of the mouthpiece casing 15. The hollow of the support comprises a longitudinal, central channel 23 through the length of the support 20. The channel 23 has a square cross-sectional shape, the cross-section being perpendicular to the longitudinal axis of the support.

The support 20 acts as a wicking element, as it is configured to wick liquid in the direction W from the liquid store 6 of the mouthpiece 2 to the heating element 21. For example, the porous material of the support 20 may be nickel foam, wherein the porosity of the foam is such that the described wicking occurs. Once liquid wicks W from the liquid store 6 to the support 20, it is stored in the porous material of the support 20. Thus, the support 20 is an extension of the liquid store 6.

The heating element 21 is formed of a single wire and comprises a heating element coil 24 and two leads 25, as is illustrated in FIGS. 3, 5, 6 and 7. For example, the heating element 21 may be formed of Nichrome. The coil 24 comprises a section of the wire where the wire is formed into a helix about an axis A. At either end of the coil 24, the wire departs from its helical form to provide the leads 25. The leads 25 are connected to the electrical contacts 26 and are thereby configured to route electrical power, provided by the power cell 9, to the coil 24.

Figure 3:
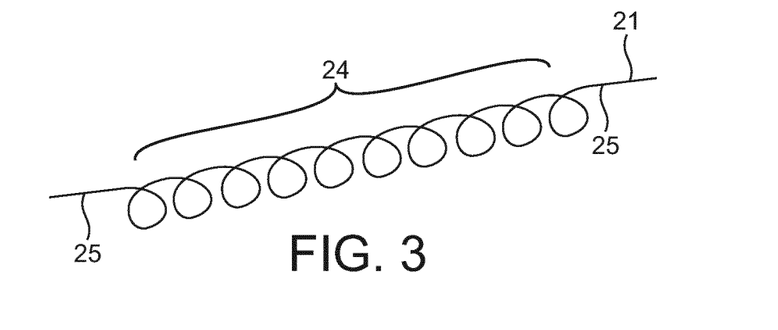
FIG. 3 is a side perspective view of a heating element coil.
Figure 4:
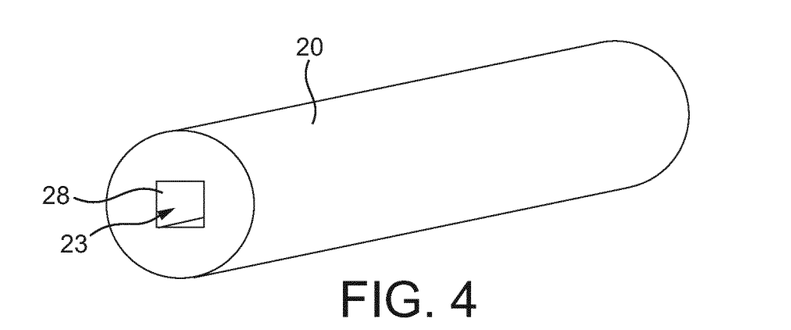
FIG. 4 is a side perspective view of an outer heating element support.

The wire of the coil 24 is approximately 0.12 mm in diameter. The coil is approximately 25 mm in length, has an internal diameter of approximately 2 mm and a helix pitch of approximately 420 micrometers. The void between the successive turns of the coil is therefore approximately 300 micrometers.

The coil 24 of the heating element 21 is located coaxially within the channel 23 of the support. The heating element coil 24 is thus coiled within the channel 23 of the heating element support 20. Moreover, the axis A of the coil 24 is thus parallel to the cylindrical axis B of the mouthpiece casing 15 and the longitudinal axis C of the electronic cigarette 1. Moreover, the device 1 is configured such that the axis A of the coil 24 is substantially parallel to airflow F through the device when a user sucks on the device. Use of the device 1 by a user is later described in more detail.

Figure 5:
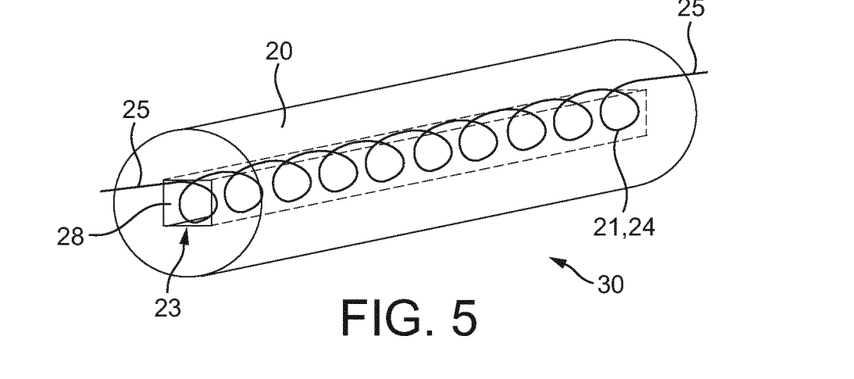
FIG. 5 is a side perspective view of a heating element coil within an outer heating element support.
Figure 6:
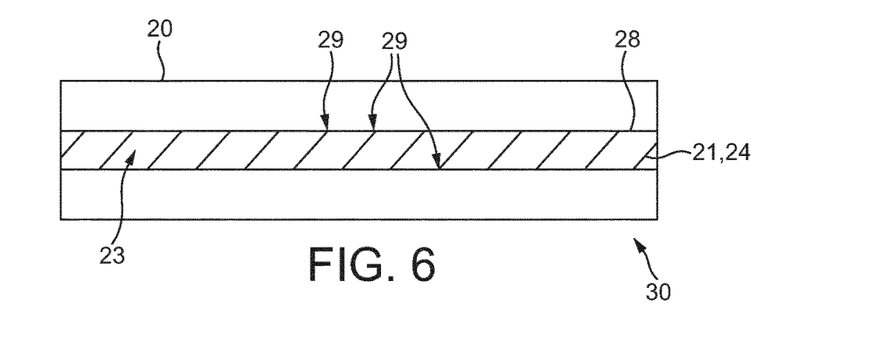
FIG. 6 is a side sectional view of a heating element coil within an outer heating element support.
Figure 7:
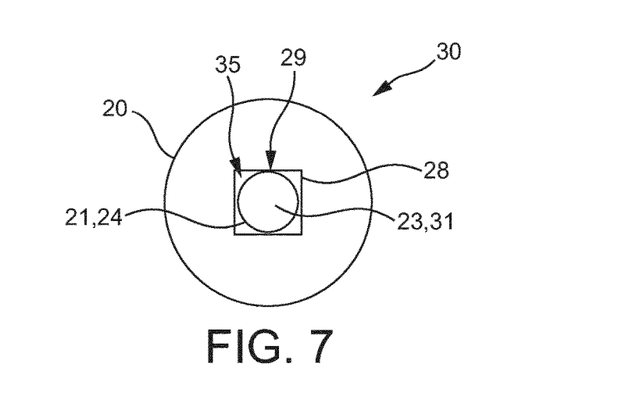
FIG. 7 is an end view of a heating element coil within an outer heating element support, where a central channel has a square cross-section.

The coil 24 is the same length as the support 20, such that the ends of the coil 24 are flush with the ends of the support 20. The outer diameter of the helix of the coil 24 is similar to the cross-sectional width of the channel 23. As a result, the wire of the coil 24 is in contact with the surface 28 of the channel 23 and is thereby supported, facilitating maintenance of the shape of the coil 24. Each turn of the coil is in contact with the surface 28 of the channel 23 at a contact point 29 on each of the four walls 28 of the channel 23. The combination of the coil 24 and the support 20 provides a heating rod 30, as illustrated in FIGS. 5, 6 and 7. The heating rod 30 is later described in more detail with reference to FIGS. 5, 6 and 7.

The inner surface 28 of the support 20 provides a surface for liquid to wick onto the coil 24 at the points 29 of contact between the coil 24 and the channel 23 walls 28. The inner surface 28 of the support 20 also provides surface area for exposing wicked liquid to the heat of the heating element 21.

Figure 8:
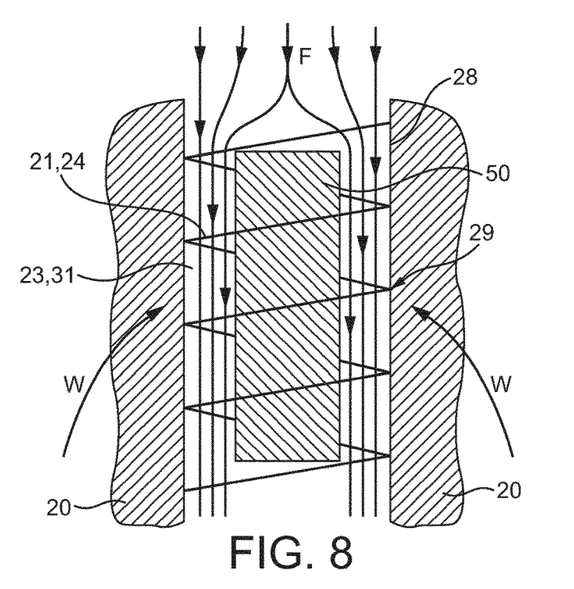
FIG. 8 is a side view of a coil and a cylindrical airflow channeler.

The airflow channeler 50 is cylindrical in shape, with a diameter smaller than that of the coil 24, and is located coaxially within the coil 24 as shown in FIG. 8. The airflow channeler 50 is configured to influence the path of airflow through the vaporisation cavity 19 when a user sucks on the device. The influence of the airflow channeler 50 on the path of the airflow is described in more detail later. The channeler 50 may for example be secured in place by suitable connectors, it may be allowed to be retained freely in the heater element 21, or the heater 21 may be designed so as to retain the channeler 50. The airflow channeler 50 may for example be formed of ceramic material.

There exists a continuous inner cavity 31 within the electronic cigarette 1 formed by the adjacent hollow interiors' of the mouthpiece casing 15 and the battery assembly casing 8.

In use, a user sucks on the second end 17 of the mouthpiece casing 15. This causes a drop in the air pressure throughout the inner cavity 31 of the electronic cigarette 1, particularly at the air outlet 4.

The pressure drop within the inner cavity 31 is detected by the pressure sensor 13. In response to detection of the pressure drop by the pressure sensor 13, the controller 14 triggers the provision of power from the power cell 9 to the heating element 21 via the electrical contacts 10, 26. The coil of the heating element 21 therefore heats up. Once the coil 24 heats up, liquid in the vaporisation cavity 19 is vaporised. In more detail, liquid on the coil 24 is vaporised, liquid on the inner surface 28 of the heating element support 20 is vaporised and liquid in the portions 22 of the support 20 which are in the immediate vicinity of the heating element 21 may be vaporised. Moreover, liquid may have gathered on the airflow channeler 50 and this liquid may also be vaporised.

The pressure drop within the inner cavity 31 also causes air from outside of the electronic cigarette 1 to be drawn, along route F, through the inner cavity from the air inlet 27 to the air outlet 4. As air is drawn along route F, it passes through the vaporisation cavity 19, picking up vaporised liquid, and the air passageway 18. The vaporised liquid is therefore conveyed along the air passageway 18 and out of the air outlet 4 to be inhaled by the user.

As the air containing the vaporised liquid is conveyed to the air outlet 4, some of the vapour may condense, producing a fine suspension of liquid droplets in the airflow. Moreover, movement of air through the vaporiser 7 as the user sucks on the mouthpiece 2 can lift fine droplets of liquid off of the heating element 21 and/or the heating element support 20. The air passing out of the air outlet 4 may therefore comprise an aerosol of fine liquid droplets as well as vaporised liquid.

The airflow path F passes through the channel 23 of the support 20. This involves the airflow travelling along the length of the coil 24, both within and outside of the circumference of the coil 24. The airflow channeler 50 influences the passage of the airflow through the channel 23 such that the airflow is restricted to an air passageway 51 about the channeler 50 having an annular cross-section and encompassing the wire of the coil 24. The airflow channeler 50 therefore causes a venturi effect, whereby restricting the airflow to the annular passageway 51 causes an increase in the speed of the airflow and a decrease in the static pressure of the airflow.

Restricting the airflow to the annular passageway 51 improves the efficiency of the vaporiser 7 as airflow is forced to pass close to the wire of the coil 24. Moreover, the increase in the speed of the airflow over the coil 24, caused by the channeler 50, can result in an increased rate of vaporisation. The channeler 50 also influences the wicking of liquid, as the decrease in the static pressure at the surface 28 of the channel 23 causes an increase in the wicking of liquid from the liquid store 6 to the support 20, and from the support 20 to the coil 24. The airflow channeler 50 therefore facilitates an increase in the amount of vapour delivered to the outlet 4 for a given volume of airflow through the device 1.

With reference to FIGS. 5, 6 and 7, due to the cross-sectional shape of the channel 23, gaps 35 are formed between the inner surface 28 of the heating element support 20 and the coil 24. In more detail, where the wire of the coil 24 passes between contact points 29, a gap 35 is provided between the wire and the area of the inner surface 28 closest to the wire due to the wire substantially maintaining its helical form. The distance between the wire and the surface 28 at each gap 35 is in the range of 10 micrometers to 500 micrometers. The gaps 35 are configured to facilitate the wicking of liquid onto the coil 24 through capillary action at the gaps 35. The gaps 35 also provide areas in which liquid can gather prior to vaporisation, and thereby provide areas for liquid to be stored prior to vaporisation. The gaps 35 also expose more of the coil 24 for increased vaporisation in these areas.

Many alternatives and variations to the embodiments described above are possible. For instance, FIGS. 9 to 15 show other airflow channeler 50 configurations.

Figure 9:
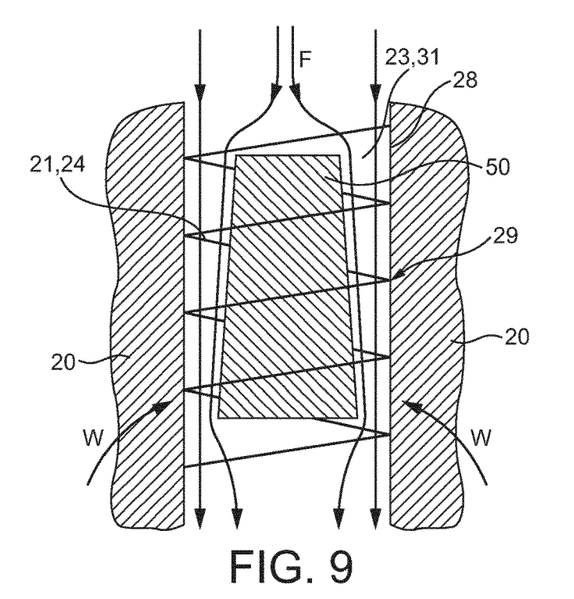
FIG. 9 is a side view of a coil and a conical airflow channeler.
Figure 10:
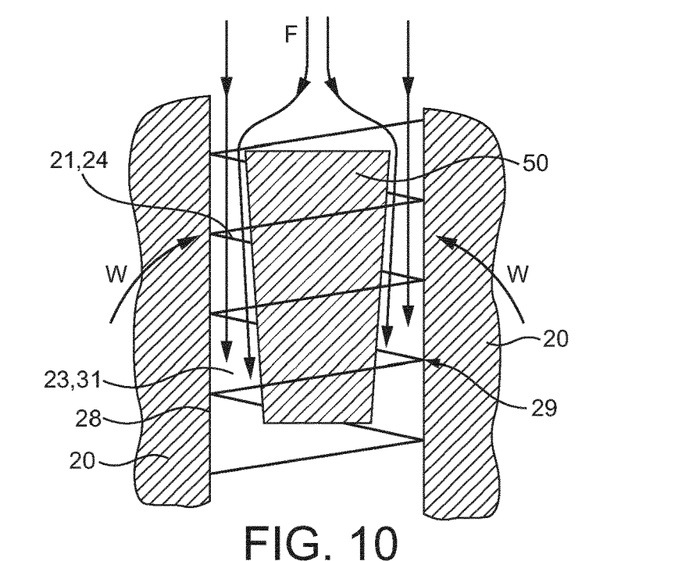
FIG. 10 is a side view of a coil and an inverted conical airflow channeler.
Figure 11:
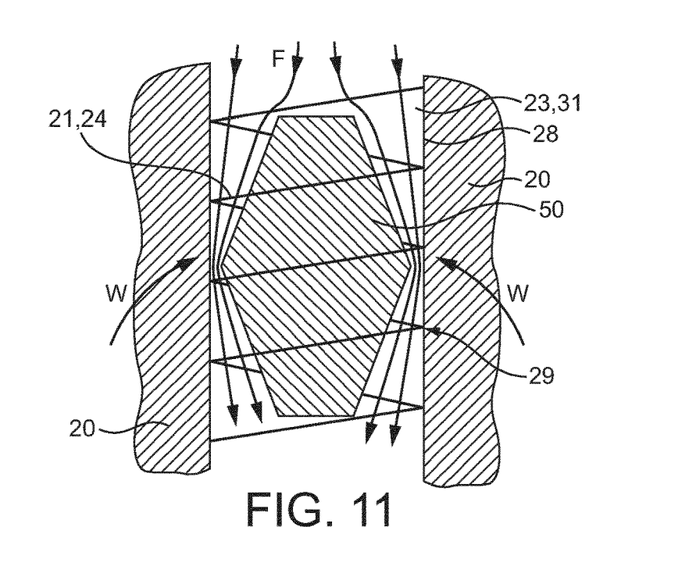
FIG. 11 is a side view of a coil and an airflow channeler with a central bulge.

FIGS. 9 to 11 each show an airflow channeler 50 situated within the coil 24 in order to obstruct the airflow within the coil 24 and direct the airflow to different points on the coil 24 surface. In each of FIGS. 9 to 11, the channeler 50 prevents air flowing through the coil 24 in a central region, restricting the airflow to a substantially annular passageway 51 about the channeler 50 encompassing the wire of the coil. Moreover, the effects of the channeler 50, on the vaporiser 7 efficiency and the wicking of liquid, described with reference to FIG. 8 apply similarly to the channeler 50 configurations of FIGS. 9 to 11.

In FIG. 9, the airflow channeler 50 has a conical shape where the height dimension H of the cone is coaxial with the coil 24. Moreover, the channeler 50 is situated within the coil 24 such that the direction F of airflow in use leads from a narrower section of the cone to a wider section of the cone.

Due to the conical shape of the channeler 50, the cross-sectional area of the annular passageway 51 decreases as the air moves along the channeler 50. As the air flows along the cone leading from a narrower to a wider section, it is increasingly directed towards the surface of the coil 24. Moreover, the venturi effect caused by the channeler 50 increases as air moves along the channeler 50. It therefore builds up an airflow speed and pressure gradient over the coil surface towards the base of the coil. As a result, the rate of vaporisation increases as the air passes along the passageway 51. Furthermore, the increased wicking caused by the channeler 50 increases towards the narrowest point of the passageway 51.

In FIG. 10, the airflow channeler 50 has an inverted conical shape compared to that of FIG. 9, where the height dimension H of the cone is coaxial with the coil 24. The direction of airflow in use leads from a wider cone section to a narrower cone section.

Due to the conical shape of the channeler 50, the cross-sectional area of the annular passageway 51 increases as the air moves along the channeler 50. The airflow is directed closer to the coil 24 surface at the start of the path and less so as the air flows down the cone sides. This creates an airflow speed and pressure gradient over the coil 24 surface. The airflow path follows the shape of the cone and as the cone narrows acts to draw vapour towards the centre of the coil 24 and away from the coil surface.

In FIG. 11, the airflow channeler 50 has a generally cylindrical shape bulging in a central region 52, and is coaxial with the coil 24. The direction of airflow in use leads along the channeler 50 from a narrower section at one end of the channeler 50 to the wider central bulge section 52 and back to a narrower section at the other end of the channeler 50.

Due to the conical shape of the channeler 50, the cross-sectional area of the annular passageway 51 decreases and then increases again as the air moves along the channeler 50. The airflow is directed closer to the coil 24 surface at a central region 52 and then away from the coil surface past the central region 52. The airflow is therefore focused on the central coil region. This creates two airflow gradients, one before the bulge and one after it. The airflow in the annular passageway 51 is therefore fastest at the bulge 52. Moreover, the static pressure at the surface 28 of the channel 23 is lowest in the vicinity of the bulge 52. Wicking of liquid to the heating element 21 is therefore highest in the vicinity of the bulge 52.

Figure 12:
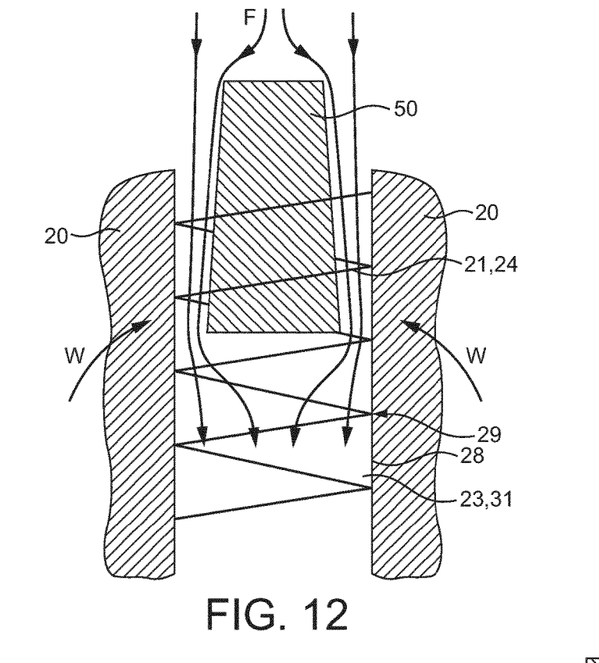
FIG. 12 is a side view of a coil and an airflow channeler partially outside the coil.

The example shown in FIG. 12 is similar to that of FIG. 9 with the exception that the airflow channeler 50 is partially outside the coil 24, such that wider end of the cone lies within the coil 24. As the air flows along the outside of the cone surface it is directed closer to the coil 24 surface, its speed increases and its static pressure decreases. Once the airflow passes the channeler 50 it enters an unobstructed region 53 within the coil 24. As the airflow passes into the unobstructed region 53, it is drawn towards the central region of the coil 24 and thereby draws vapour away from the coil 24 surface.

Figure 13:
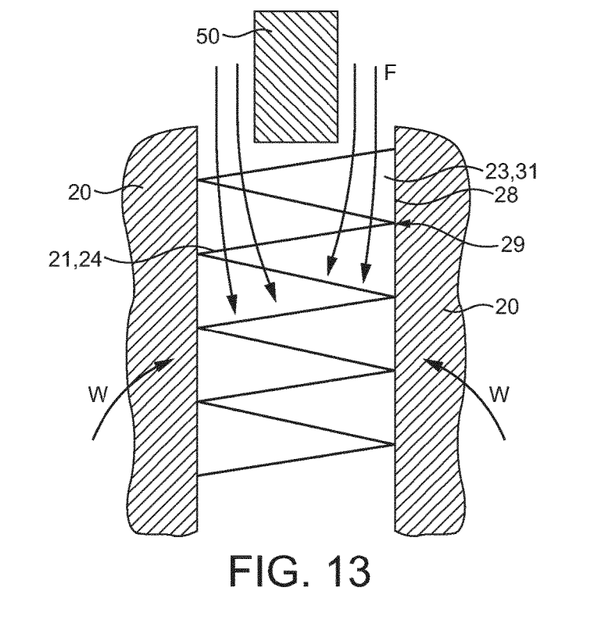
FIG. 13 is a side view of a coil and an airflow channeler outside of the coil.

In FIG. 13 the airflow channeler 50 is situated outside of the coil 24. In this example the airflow channeler 50 is a cylinder and is located such that it is coaxial with the coil 24. The airflow channeler 50 causes an obstruction such that air flows down the side of the cylinder and is incident on the ends of the coil 24. The airflow passes through the coil turns and in the absence of an obstruction within the coil 24, the airflow moves towards the inner coil 24 section taking vapour with it.

Figure 14:
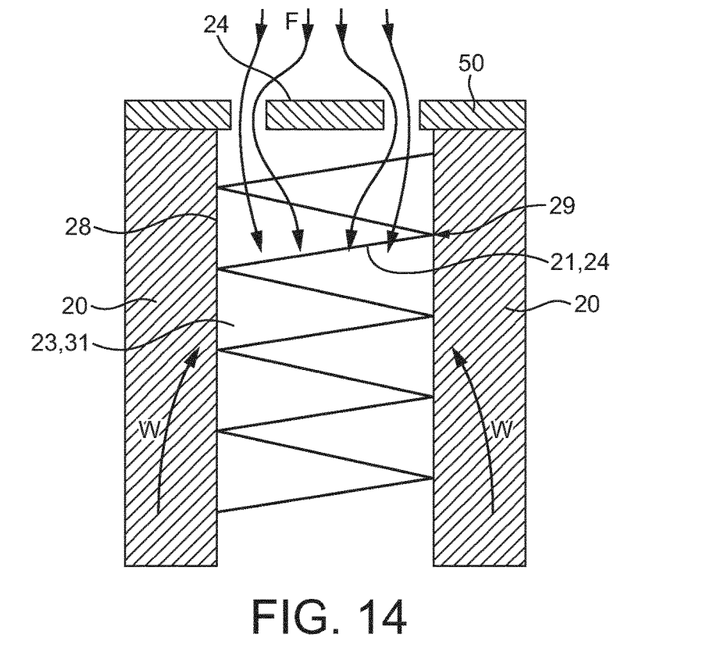
FIG. 14 is a side view of a coil and an airflow channeler forming part of a heating element support.
Figure 15:
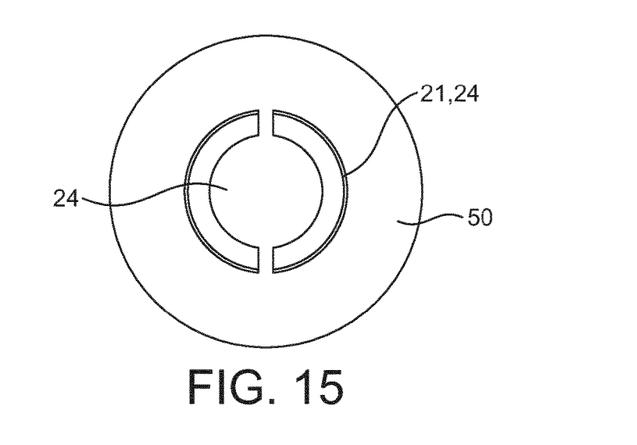
FIG. 15 is an end view of an airflow channeler forming part of a heating element support.

FIGS. 14 and 15 show another example configuration of an airflow channeler 50. The airflow channeler 50 is an end cap 50, or plate 50, located over a first end of the channel 23. Moreover, the channeler 50 has an annular aperture 55 aligned with the annular profile of the coil 24. The end cap 50 determines how the air enters the channel 23 in that air can only flow through the annular aperture 55 onto the coil 24 end. Thus, airflow is drawn over the coil end and through the coil turns. Once the airflow has passed the end cap 50 it can flow into the central region of the coil 24. In use, this flow through the end of the coil 24 and the coil turns and into the centre of the coil 24 acts to efficiently remove vapour from the coil 24 to be inhaled by the user. The end cap channeler 50 may form part of the heating element support 20.

Although examples have been shown and described it will be appreciated by those skilled in the art that various changes and modifications might be made without departing from the scope of the invention.

The airflow channeler 50 may be configured to channel the airflow such that the airflow over wire of the coil 24 is fastest at a point where liquid is provided to the coil 24.

An electronic vapour provision device 1 comprising an electronic cigarette 1 is described herein. However, other types of electronic vapour provision device 1 are possible.

The electronic vapour provision device 1 may be configured such that the axis A of the coil is at an angle to a longitudinal axis of the electronic vapour provision device 1. For example, the components of the device 1 may be configured such that the coil is perpendicular to the longitudinal axis of the electronic vapour provision device 1 and such that air flow F over the coil when a user sucks on the mouthpiece is substantially parallel to the coil axis.

An air pressure sensor 13 is described herein. In embodiments, an airflow sensor may be used to detect that a user is sucking on the device 1.

The electronic vapour provision device 1 is not restricted to the sequence of components described and other sequences could be used such as the control circuit 11 being in the tip of the device 1 or the liquid store 6 being in the body 3 rather than the mouthpiece 2.

The electronic vapour provision device 1 of FIG. 2 is described as comprising two detachable parts, the mouthpiece 2 and the body 3, comprising the battery assembly 5. Alternatively, the device 1 may be configured such these parts 2, 5 are combined into a single integrated unit. In other words, the mouthpiece 2 and the body 3 may not be detachable.

The distance between the wire and the surface 28 at each gap 35 is described above as being in the range of 10 micrometers to 500 micrometers. However, other gap sizes are possible.

The wire of the coil 24 is described above as being approximately 0.12 mm thick. However, other wire diameters are possible. For example, the diameter of the coil 24 wire may be in the range of 0.05 mm to 0.2 mm. Moreover, the coil 24 length may be different to that described above. For example, the coil 24 length may be in the range of 20 mm to 40 mm.

The internal diameter of the coil 24 may be different to that described above. For example, the internal diameter of the coil 24 may be in the range of 0.5 mm to 2 mm.

The pitch of the helical coil 24 may be different to that described above. For example, the pitch may be between 120 micrometers and 600 micrometers.

Furthermore, although the distance of the voids between turns of the coil 24 is described above as being approximately 300, different void distances are possible. For example, the void may be between 20 micrometers and 500 micrometers.

The size of the gaps 35 may be different to that described above.

The heating element is not restricted to being a uniform coil.

Airflow channelers 50 having other shapes could be used to achieve different airflow requirements. Moreover, any of the example shapes described as airflow channelers 50 within the coil could be only partially within the coil or situated outside the coil.

Where the end cap 50 forms an obstruction, apertures 55 of different shapes could be used to create different incident airflows.

The airflow channeler 50 is not restricted to channeling the airflow through a coil and could, for example, be arranged to channel airflow on to the side of a coil or heating element.

Where a heating element support is utilised this is not restricted to being an outer support and could be an inner support. An inner support could have a dual function as a support and as an airflow channeler 50, adopting any of the example shapes.

Reference herein to a vaporisation cavity 19 may be replaced by reference to a vaporisation region.

In order to address various issues and advance the art, the entirety of this disclosure shows by way of illustration various embodiments in which the claimed invention(s) may be practiced and provide for superior electronic vapour provision. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilised and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future. Any feature of any embodiment can be used independently of, or in combination with, any other feature.

The invention claimed is:

1. An electronic vapor provision device having a longitudinal axis, the electronic vapor provision device comprising a power cell and a vaporizer provided in a casing comprising an air inlet, the vaporizer including a heater and a vaporization cavity configured such that, in use, an airflow travels along the longitudinal axis of the electronic vapor provision device towards the vaporizer, the vaporizer further including a heater support within the casing, wherein the heater is on an inside of the heater support, and an airflow channeler, the airflow channeler being distinct from the heater support and configured, in use, to direct the airflow toward the heater by acting as an obstruction to prevent the airflow from flowing along the longitudinal axis of the electronic vapor provision device.

2. The electronic vapor provision device of claim 1, wherein the electronic vapor provision device is an electronic cigarette.

3. The electronic vapor provision device of claim 1, wherein the airflow channeler is configured, in use, to direct airflow along a length of the heater.

4. The electronic vapor provision device of claim 1, wherein the airflow channeler is configured, in use, to focus airflow in one or more regions of the heater.

5. The electronic vapor provision device of claim 4, wherein the airflow channeler is configured, in use, to focus airflow in an end region of the heater or in a central region of the heater.

6. The electronic vapor provision device of claim 1, wherein the airflow channeler is configured, in use, to create an airflow gradient over the heater.

7. The electronic provision device of claim 1, wherein the airflow channeler is situated at least partly within the vaporization cavity.

8. The electronic vapor provision device of claim 7, wherein the airflow channeler provides an obstruction in the vaporization cavity such that, in use, airflow is channeled over the heater.

9. The electronic vapor provision device of claim 1, wherein the airflow channeler is situated outside of the vaporization cavity.

10. The electronic vapor provision device of claim 1, wherein at least part of the airflow channeler is situated within the heater.

11. The electronic vapor provision device of any one of claim 1, wherein the airflow channeler is situated outside of the heater.

12. The electronic vapor provision device of claim 1, wherein the airflow channeler is elongated in the direction of a longitudinal axis of the heater.

13. The electronic vapor provision device of claim 1, wherein a cross-sectional shape of the airflow channeler is a polygon substantially polygonal.

14. The electronic vapor provision device of claim 13, wherein the cross-sectional shape of the airflow channeler is substantially square.

15. The electronic vapor provision device of claim 1, wherein the airflow channeler comprises a spiral shape.

16. The electronic vapor provision device of preceding claim 1, wherein the airflow channeler is substantially conical.

17. The electronic vapor provision device of claim 1, wherein the airflow channeler is cylindrical.

18. The electronic vapor provision device of claim 1, wherein the airflow channeler comprises a wider end and a narrower end and is configured such that, in use, air is drawn towards the wider end or the narrower end.

19. The electronic vapor provision device of claim 1, wherein the airflow channeler is shaped so as to bulge in one or more regions.

20. The electronic vapor provision device of claim 19, wherein the airflow channeler is shaped so as to bulge in a central region.

21. The electronic vapor provision device of claim 1, wherein the heater is a heater coil.

22. The electronic vapor provision device of claim 21, wherein the airflow channeler is configured, in use, to spiral airflow over the heater coil.

23. The electronic vapor provision device of claim 21, wherein the airflow channeler is configured, in use, to focus airflow on an end of the heater coil, an inside of the heater coil or an outside of the heater coil.

24. The electronic vapor provision device of claim 21, wherein the airflow channeler is configured, in use, to focus airflow through turns of the heater coil.

25. The electronic vapor provision device of claim 1, wherein the heater is not supported on its inside.

26. The electronic vapor provision device of claim 1, wherein the heater support is a liquid store.

27. The electronic vapor provision device of claim 1, wherein one or more gaps are provided between the heater and the heater support.

28. The electronic vapor provision device of claim 1, wherein the heater is in contact with the heater support at points along a length of the heater support.

29. The electronic vapor provision device of claim 1, wherein the electronic vapor provision device further comprises a mouthpiece section and the vaporizer is part of the mouthpiece section.

30. The electronic vapor provision device of claim 29, further comprising a heater support that substantially fills the mouthpiece section.

31. The electronic vapor provision device of claim 1, further comprising:
    a liquid store configured to provide liquid to the heater for vaporization; and
    a vapor outlet for liquid vaporized by the heater.

32. The electronic vapor provision device of claim 31, wherein the liquid store is situated within the casing.

* * * * *